(12) United States Patent
Reyes

(10) Patent No.: US 6,803,060 B2
(45) Date of Patent: Oct. 12, 2004

(54) COMPOSITION TO BOOST LIBIDO

(76) Inventor: Joe Reyes, 1175 Chicago Rd., Troy, MI (US) 48083

( * ) Notice: Subject to any disclaimer, the term of this patent is extended or adjusted under 35 U.S.C. 154(b) by 0 days.

(21) Appl. No.: 09/927,995

(22) Filed: Aug. 10, 2001

(65) Prior Publication Data
US 2002/0068728 A1 Jun. 6, 2002

Related U.S. Application Data
(60) Provisional application No. 60/230,656, filed on Sep. 7, 2000.

(51) Int. Cl.⁷ .................. A61K 35/78; A61K 31/56; A61K 31/355; A61K 31/195
(52) U.S. Cl. .................. 424/769; 424/757; 424/725; 424/195.1; 514/177; 514/178; 514/181; 514/458; 514/561
(58) Field of Search ................ 514/177, 178, 514/181, 249, 256, 258, 257, 261, 262, 561, 458; 424/195.1, 769, 757, 725

(56) References Cited

U.S. PATENT DOCUMENTS

| | | |
|---|---|---|
| 3,943,246 A | 3/1976 | Sturmer |
| 4,127,118 A | 11/1978 | Latorre |
| 4,139,617 A | 2/1979 | Grunwell et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,530,920 A | 7/1985 | Nestor et al. |
| 4,801,587 A | 1/1989 | Voss et al. |
| 4,863,911 A | 9/1989 | Anderson et al. |
| 4,885,173 A | 12/1989 | Stanley et al. |
| 4,925,678 A | 5/1990 | Ranney |
| 4,959,217 A | 9/1990 | Sanders et al. |
| 5,059,603 A | 10/1991 | Rubin |
| 5,065,744 A | 11/1991 | Zumanowsky |
| 5,167,616 A | 12/1992 | Haak et al. |
| 5,169,383 A | 12/1992 | Gyory et al. |
| 5,225,182 A | 7/1993 | Sharma |
| 5,516,516 A * | 5/1996 | Cherksey ............... 424/773 |
| 6,093,421 A * | 7/2000 | DeLuca et al. ............ 424/543 |

OTHER PUBLICATIONS

TriBex–500 (First Use in Commerce in Mar. 30, 1998, the record of the Trademark in USPTO).*
ArginMax (First Use in Commerce in Apr. 1, 1998, the record of the Trademark in USPTO).*
Hardman et al. "Goodman & Gilman's The Pharmacological Basis of Therapeutics" (9th ed, 1996) p. 51.*
Webster's II New Riverside University Dictionary 1994, p. 785.*
Reid, Daniel, "A Handbook of Chinese Healing Herbs" 1995, Barnes & Noble, pp. 243–246.*
Althof et al. J. Sex Marital Ther. 17(2): 101–112 (1991).
Brindley, G.S., Br. J. Psychiatr. 143:332–337 (1983).
Brindley, G. S. (Br. J. Pharmac. 87:495–500, 1986).
Brindley, J. Physiol. 342:24P (1983).
Corriere, et al., J. Urol. 140:615–617 (1988).
Gwinup, Ann. Int. Med. Jul. 15, 1988, pp. 162–163.
Kolodny et al., Textbook of Sexual Medicine, Little and Brown, Boston, Mass. (1979).
Larsen, et al., J. Urol. 137:292–293 (1987).
Oral Sildenafil in the Treatment of Erectile Dysfunction, New England Journal of Medicine, 338:20:1397 (1998).
Sonda et al. J. Sex & Martial Ther. 16(1): 15–21 (year).
Virag, et al., Angiology 35:79–87 (1984).
Virag, Lancet ii:938 (1982).
Zorgniotti et al., J. Urol. 133:39–41 (1985).

* cited by examiner

Primary Examiner—Shaojia Anna Jiang
(74) Attorney, Agent, or Firm—Kenneth I. Kohn; Amy E. Rinaldo; Kohn & Associates, PLLC

(57) ABSTRACT

There is provided a natural composition for boosting the libido of an individual, the composition including an effective amount of an aphrodisiac and a compound to increase blood flow to the pelvic area in a pharmaceutically acceptable carrier. A natural composition for boosting the libido of an individual, including an effective amount of a compound for driving blood flow to the penis and an aphrodisiac in a pharmaceutically acceptable carrier is also provided. Also provided is a method of increasing the libido by administering an effective amount of composition including an aphrodisiac and a compound to increase blood flow to the pelvic area in a pharmaceutically acceptable carrier.

3 Claims, No Drawings

COMPOSITION TO BOOST LIBIDO

CROSS REFERENCE TO RELATED APPLICATIONS

This applications claims the benefit of priority under 35 U.S.C. Section 119(e) of U.S. Provisional Patent Application No. 60/230,656, filed Sep. 7, 2000, which is incorporated herein by reference.

BACKGROUND OF THE INVENTION

1. Technical Field

The present invention relates to herbal compositions and there method of use. More specifically, the present invention relates to the use of such a composition to boost a person's libido.

2. Description of Related Art

The human sexual response in both males and females results from a complex interplay of psychological, hormonal, and other physiological influences. One important aspect of human sexual response that is common to both men and women is the erectile response which itself results from an interplay between the autonomic nervous system, the endocrine system, and the circulatory system.

Finding a suitable drug delivery vehicle for the treatment of erectile dysfunction has proven to be particularly difficult. Male erectile dysfunction, the persistent inability of a man to achieve or maintain an erection sufficient for satisfactory sexual performance, is estimated to affect up to 30 million men in the United States. See "Oral Sildenafil in the Treatment of Erectile Dysfunction", New England Journal of Medicine, 338:20:1397 (1998). There are numerous causes of male erectile dysfunction. For example, it may be atonic, due to paralysis of the motor nerves without any evidence of lesions to the central nervous system, particularly the spinal cord. Alternatively, it could be psychic, and dependent on a mental problem or instability. Finally, it could be symptomatic, due to some other disorder, such as injury to nerves in the perineal region, by virtue of which the sensory portion of the erection reflex is blocked out.

Various available treatments have been employed in the treatment of male erectile dysfunction, including vacuum-constriction devices, intracavernosal injections of vasoactive agents, transurethral delivery of prostaglandin E.sub.1 (alprostadil), oral administration of sildenafil citrate (Viagra.RTM. available from Pfizer), implantation of penile prostheses, and venous or arterial surgery. Most of these treatments involve painful procedures with varying degrees of success that are often associated with numerous side effects. Moreover, many persons are not candidates for one or more of these treatments as a result of their physiological condition. For example, oral admistration of sildenafil citrate is contraindicated for individuals currently taking organic nitrates, such a nitroglycerine. See "VIAGRA.RTM. (sildenafil citrate) Tablets", Pfizer Labs, 7 (1998).

The medications most commonly used to treat male erectile dysfunction have been papaverine hydrochloride, a smooth muscle relaxant, phentolamine mesylate, an alpha-adrenergic blocker, and several other drugs which are used because of their ability to cause vasodilation. Recent data have suggested that prostaglandin $E_1$ either alone or in combination with papaverine produces an improved erectile response. The use of these drugs often requires special applicators, which besides being cumbersome, are also painful to use. However, the use of topical gels, creams and ointments for treating impotency has been proposed in several publications.

Numerous approaches have been taken in attempts to treat impotence. These approaches include the use of external or internally implanted penile prosthesis. (See, e.g., U.S. Pat. No. 5,065,744, to Zumanowsky). A variety of drugs and methods for administering drugs have also been used in attempts to treat impotence. For example, U.S. Pat. No. 3,943,246 to Sturmer addresses treatment of impotence in men by buccal and peroral administration of daily doses of 300–1500 international units (I.U.) of oxytocin or daily divided doses of 150–250 I.U. of desamino-oxytocin. The patent discloses the buccal administration of 100 I.U. three times a day for 14 days results in improvement of impotentia erectionis in 12 of the 16 patients treated.

U.S. Pat. No. 4,530,920 to Nestor et al. discloses that the administration of nonapeptide and decapeptide analogs of luteinizing hormone releasing hormone agonists may be useful in the induction or enhancement of sexual behavior or therapy for impotence or frigidity. Nestor et al. suggest numerous routes of administration of the analogs including buccal, sublingual, oral, parenteral (including subcutaneous, intramuscular, and intravenous administration), rectal, vaginal, and others.

U.S. Pat. No. 4,139,617 to Grunwell et al. suggests buccal and other routes of administration of 19-oxygenated-androst-5-enes for the endocrine mediated enhancement of the libido in humans.

U.S. Pat. No. 4,863,911 to Anderson et al. discloses methods for treating sexual dysfunction in mammals using a biooxidizable, blood-brain barrier penetrating estrogen derivative. One of the purported objects of the Anderson et al. invention is the treatment of "psychological impotence" in males. Test results showed that the drugs used in the study stimulated mounting behavior, intromission, and mount latency in castrated rats.

A number of publications have proposed the use of various vasodilators for the treatment of impotence in males. Attempts to utilize vasodilators for the treatment of impotence were prompted by the fact that a significant percentage of cases of impotence were noted to be vasculogenic, i.e. resulting from vascular insufficiency.

Voss et al., U.S. Pat. No. 4,801,587, issued Jan. 31, 1989, discloses the use of an ointment containing a vasodilator and a carrier agent for topical application to the penis of impotent men. The Voss et al. patent also describes application of such an ointment into the urethra of the penis using a catheter as well as a multi-step regimen for applying a vasodilator to the skin of the penis. In addition, Voss et al. proposes the surgical removal of a portion of the fibrous sheath surrounding the corpora cavernosum, thereby facilitating the penetration of a vasodilator-containing ointment into the corpora cavernosum. Vasodilators disclosed for use by Voss et al. include papaverine, hydralazine, sodium nitroprusside, phenoxybenzamine, and phentolamine. The Voss et al. patent, however, provides no information regarding the actual efficacy of the treatments proposed or the nature of the response to such treatments.

U.S. Pat. No. 4,127,118 to Latorre describes treating male impotence by direct injection of the vasodilating drugs into the corpus cavernosum and the corpus spongiosum of the penis using a syringe and one or more hypodermic needles. More particularly, the Latorre patent proposes the intracavernosal and intraspongiosal injection of sympathomimetic amines such as nylidrin hydrochloride, adrenergic blocking agents such as tolazoline hydrochloride, and direct acting vasodilators such as isoxsuprine hydrochloride and nicotinyl alcohol.

Brindley, G. S. (Br. J. Pharmac. 87:495–500, 1986) disclosed that, when injected directly into the corpus cavernosum using a hypodermic needle, certain smooth muscle relaxing drugs including phenoxybenzamine, phentolamine, thymoxamine, imipramine, verapamil, papaverine, and naftidrofuryl caused erection. This study noted that injection of an "appropriate dose of phenoxybenzamine or papaverine is followed by an unrelenting erection lasting for hours." Injection of the other drugs studied induced erections lasting from about 11 minutes to about 6.5 hours.

Zorgniotti et al., J. Urol. 133:39–41 (1985) demonstrated that the intracavernosal injection of a combination of papaverine and phentolamine could result in an erection in otherwise impotent men. Similarly, Althof et al. J. Sex Marital Ther. 17(2): 101–112 (1991) reported that intracavernosal injection of papaverine hydrochloride and phentolamine mesylate resulted in improved erectile ability in about 84% of patients injected. However, in that study the dropout rate was 57%, fibrotic nodules developed in 26% of the patients, 30% of the patients developed abnormal liver function values, and bruising occurred in 19% of the patients.

Other studies describing intracavernosal injection of drugs using hypodermic needles for the treatment of impotence include: Brindley, J. Physiol. 342:24P (1983); Brindley, Br. J. Psychiatr. 143:312–337 (1983); Virag, Lancet ii:978 (1982); and Virag, et al., Angiology 35:79–87 (1984).

While intracavernosal injection may be useful for inducing erections in impotent men, the technique has numerous drawbacks. Obvious drawbacks include pain, risk of infection, inconvenience and interference with the spontaneity of the sex act. Priapism (prolonged and other painful erection) also appears to be a potential problem when using injection methods. See, e.g. Brindley, (1986). Another problem arising in some cases of intracavernosal injection involves the formation of fibrotic lesions in the penis. See, e.g., Corriere, et al., J. Urol. 140:615–617 (1988) and Larsen, et al., J. Urol. 137:292–293 (1987).

Phentolamine, which has been shown to have the potential to induce erection when injected intracavernosally, has also been the subject of oral administration to test its effects in men having non-specific erectile insufficiency (Gwinup, Ann. Int. Med. Jul. 15, 1988, pp. 162–163.) In that study, 16 patients ingested either a placebo or a 50 mg orally administered dose of phentolamine. Eleven of the 16 patients (including three placebo-treated patients) became tumescent, became more responsive to sexual stimulation, and were able to achieve an erection sufficient for vaginal penetration after waiting 1.5 hours to attempt intercourse.

Sonda et al. J. Sex & Marital Ther. 16(1): 15–21 (year) reported that yohimbine ingestion resulted in subjective improvement in erectile ability in 38% of impotent men treated, but only 5% of the treated patients reported complete satisfaction.

Zorgniotti et al, PCT/US94/09048, describes the transmucosal administration of a variety of vasodilators including phentolamine mesylate for modulating the human sexual response.

U.S. Pat. No. 4,885,173, to Stanley et al., discloses methods of administering drugs having cardiovascular or renal vascular activity through use of a lollipop assertedly facilitating drug absorption through the mucosal tissues of the mouth, pharynx, and esophagus. The Stanley et al. patent discloses that a large number of lollipop-administered drugs may improve cardiovascular function including drugs exhibiting direct vasodilating effects, including calcium channel blockers, .beta.-adrenergic blocking agents, serotonin receptor blocking agents, angina blocking agents, other antihypertensive agents, cardiac stimulating agents, and agents which improve renal vascular function.

U.S. Pat. No. 5,059,603 to Rubin describes the topical administration to the penis of isoxsuprine and caffeine, and nitroglycerine and caffeine along with suitable carrier compounds for the treatment of impotence.

There continues to exist a need in the art for effective means for modulating human sexual response and especially for enhancing erectile ability in males suffering from impotence. Ideally, such means would be convenient and simple to use, would be non-invasive and would allow a rapid and predictable capacity for onset of erectile function on demand and in response to normal sexual stimulation.

SUMMARY OF THE INVENTION

According to the present invention, there is provided a natural composition for boosting the libido of an individual, the composition including an effective amount of an aphrodisiac and a compound to increase blood flow to the pelvic area in a pharmaceutically acceptable carrier. A natural composition for boosting the libido of an individual, including an effective amount of a compound for driving blood flow to the penis and an aphrodisiac in a pharmaceutically acceptable carrier is also provided. Also provided is a method of increasing the libido by administering an effective amount of composition including an aphrodisiac and a compound to increase blood flow to the pelvic area in a pharmaceutically acceptable carrier.

DESCRIPTION OF THE INVENTION

Generally, the present invention provides a composition which, when ingested, will boost an individual's libido. In the preferred embodiment, the composition is taken orally. However, the composition can be administered in any other manner known to those of skill in the art. This includes, but is not limited to, intravenous, intramuscular and intraarterial administration.

By way of background, while there are obvious differences in the sexual response between men and women, one common aspect of the sexual response is the erectile response. The erectile response in both males and females is result of engorgement of the erectile tissues of the genitalia with blood in response to sexual stimulation (physical, psychological, or both).

The vasculature which serves erectile tissue in both men and women is similar. In particular, in both men and women, the arterial circulation to the erectile tissues of the genitalia derives from the common iliac artery which branches from abdominal aorta. The common iliac artery bifurcates into the internal and external iliac arteries. The internal pudic artery arises from the smaller of two terminal branches of the anterior trunk of the internal iliac artery. In the female, the internal pudic artery branches into the superficial perineal artery which supplies the labia pudenda. The internal pudic artery also branches into the artery of the bulb which supplies the bulbi vestibuli and the erectile tissue of the vagina. The artery of the corpus cavernosum, another branch of the internal pudic artery supplies the cavernous body of the clitoris. Still another branch of the internal pudic artery is the arteria dorsalis clitoridis which supplies the dorsum of the clitoris and terminates in the glans and membranous folds surrounding the clitoris which correspond to the prepuce of the male.

In the male, the internal pudic artery branches into the dorsal artery of the penis (which itself branches into a left and right branch) and the artery of the corpus cavernosum, all of which supply blood to the corpus cavernosum. The dorsal artery of the penis is analogous to the artery dorsalis clitoridis in the female, while the artery of the corpus cavernosum in the male is analogous to the artery of the same name in the female.

The male erectile response is regulated by the autonomic nervous system which controls blood flow to the penis via the interaction of peripheral nerves associated with the arterial vessels in and around the corpus cavernosum. In the non-aroused or non-erect state, the arteries serving the corpus cavernosum are maintained in a relatively constricted state, thereby limiting the blood flow to the corpus cavernosum. However, in the aroused state, the smooth muscles associated with the arteries relax under the influence of catecholamines and blood flow to the corpus cavernosum greatly increases, causing expansion and rigidity of the penis. Brindley, supra (1986) hypothesizes that smooth muscle contraction opens valves through which blood can flow from the corpus cavernosum into the extracavernosal veins. According to Brindley (1986), when the relevant smooth muscles relax, the valves close diminishing venous outflow from the corpus cavernosum. When accompanied by increased arterial blood flow into the corpus cavernosum, this results in engorgement of the corpus cavernosum and an erection.

The pre-orgasmic sexual response in females can be broken down into distinct phases. Both the excitement phase and the plateau phase involve vasodilation and engorgement (vasocongestion) of the genitalia with arterial blood in a manner analogous to the male erectile response.

The excitement phase of the female sexual response is characterized by vasocongestion in the walls of the vagina which leads to the transudation of vaginal fluids and vaginal lubrication. Further, the inner one-third of the vaginal barrel expands and the cervix and the body of the uterus become elevated. This is accompanied by the flattening and elevation of the labia majora and an increase in clitoral size. [Kolodny et al., Textbook of Sexual Medicine, Little and Brown, Boston, Mass. (1979)].

The plateau phase follows the excitement phase in the female sexual response and is characterized by prominent vasocongestion in the outer one-third of the vagina, causing a narrowing of the opening of the vagina and a retraction of the shaft and the glans of the clitoris against the symphysis pubis. These responses are also accompanied by a marked vasocongestion of the labia. [Kolodny, supra (1979)].

The vasocongestive aspects of the female sexual response are not restricted to the genitalia in that areolar engorgement also occurs, sometimes to the extent that it masks the antecedent nipple erection that usually accompanies the excitement phase.

The failure of the erectile response in men to the extent that vaginal penetration and sexual intercourse cannot be achieved is termed impotence. Impotence has numerous possible causes which can be broken down into several general classifications. Endocrine related impotence can result from primary gonadal failure, advanced diabetes mellitus, hypothyroidism, and as one of the secondary sequelae of pituitary adenoma, idiopathic or acquired hypogonadism, hyperprolactinemia and other endocrine abnormalities.

Chronic systemic illnesses such as cirrhosis, chronic renal failure, malignancies and other systemic diseases can also cause impotence. Neurogenic impotence arising in the central nervous system can be caused by temporal lobe disorders caused by trauma, epilepsy, neoplasms and stroke, intramedullary spinal lesions, paraplegia, and demyelinating disorders. Neurogenic causes of impotence arising in the peripheral nervous system include somatic or autonomic neuropathies, pelvic neoplasms, granulomas, trauma, and others. Urologic causes of impotence include complete prostatectomy, local trauma, neoplasms, Peyronie's disease, and others. In addition, as discussed above, a significant percentage of cases of impotence are vasculogenic in nature.

As many as half the cases of male impotence may be psychogenic because there is no readily-ascertainable organic cause for the disorder. Even when there appears to be an underlying organic cause of impotence, psychologic factors may play a role in the disorder.

The present invention is designed to modify all of these aspects of the erectile response on demand using vasoactive agents, aphrodisiacs, and other compounds which affect sexual function and which are administered to the circulation. The administration can be orally using a regular formulation, orally in a fast dissolving formulation, a spray formulation which can have a controlled release, a lotion, a chewable tablet, and other formulations known to those of skill in the art.

At least two different compositions are disclosed, one for women and one for men. In one embodiment of the present invention, the composition of the present invention is for administration to women. The composition includes, but is not limited to, the following: an aphrodisiac, which stimulates or intensifies sexual desire, such as Catuba Bark, a compound to increase blood flow to the pelvic area (in the preferred embodiment this causes clitoral sensitivity), such as Muria Puama, a compound to cause the body to produce natural estrogen, such as Wild Yam Root, a compound which promotes healthy sexual functioning and insures vaginal lubrication, such as Peruvian Maca, a compound to reduce vaginal dryness, such as Ipriflavone 99% (soy), a compound to create positive effects on the menstrual cycle, such as Chaste Berry, a compound which intensifies neurotransmitter pleasure, such as Avena Sativa, and a compound which increases sexual reproductive powers, such as Natural Vitamin E.

More specifically, the composition includes the following preferred compounds, which include but are not limited to: Catuaba Bark, Muria Puama, Wild Yam, Peruvian Maca, Ipriflavone (soy), Chaste Berry, Avena Sativa, and Natural Vitamin E. Other compounds having similar properties can also be used according to the present invention. Preferably, these compounds are included in the present invention in the following quantities: 290 mg Catuaba Bark, 140 mg Muria Puama, 140 mg Wild Yam, 140 mg Peruvian Maca, 96 mg Ipriflavone (soy), 66 mg Chaste Berry, 66 mg Avena Sativa, and 20 IU Natural Vitamin E.

In a second embodiment of the present invention the composition is for administration to men. The composition includes, but is not limited to, the following: a compound for increasing natural production of testosterone and elevating sperm production, such as Tribulus, a compound for driving blood flow to the penis (thus causing an erection), such as Muria Puama, an aphrodisiac, such as Catuba Bark, a compound which heightens sexual arousal, function and performance, such as Androstenedione, a compound to assist in the circulation of smooth blood flow, such as L-Arginine, a compound to boost energy and stamina, such as Korean Ginseng, a compound which intensifies neurotransmitter pleasure, such as Avena Sativa, and a compound which increases sexual reproductive powers, such as Natural Vitamin E.

More specifically, the oral composition includes the following preferred compounds, which include but are not limited to: Tribulus, Muria Puama, Catuaba Bark, Androstenedione, L-Arginine, Ginseng (Korean), Avena Sativa, and Natural Vitamin E. Preferably, these compounds are included in the present invention in the following quantities: 667 mg Tribulus, 427 mg Muria Puama, 352 mg Catuaba Bark, 127 mg Androstenedione, 127 mg L-Arginine, 60 mg Ginseng (Korean), 60 mg Avena Sativa, and 37 IU Natural Vitamin E.

A spray formulation of the present invention includes the following preferred compounds, which include but are not limited to: Tribulus terrestris, Epimedium sagattatium, Muria Puama, Serenoa reopens, Chrysin, Androstenedione, and 5-Androstenediol. Preferably, these compounds are included in the present invention in the following quantities: 35 mg Tribulus terrestris, 30 mg Epimedium sagattatium, 10 mg Muria Puama, 10 mg Serenoa reopens, 10 mg Chrysin, 7 mg Androstenedione, and 4 mg 5-Androstenediol.

The lotion formulation includes the following preferred compounds, which include but are not limited to: Tribulus terrestris, Epimedium sagattatium, 4-Androstenedione, Natural Vitamin E, and L-Arginine. These compounds are present in the lotion in a sufficient amount to improve the libido. Also included in the lotion are compounds which provide the lotion with sufficient lubrication.

The present invention provides formulations for modulating the human sexual response in a human by administering.

The present invention is specifically directed to improved methods for treating male impotence, by administering a the above described agents in an amount effective to wherein erectile ability on demand is permitted by oral administration of the above described compound.

Preferably, the amount of the above agents used in the practice of the invention for treatment of male impotence is effective to improve erectile ability in from about 1 minute to about 60 minutes following administration of the agent.

The invention is also specifically directed to methods for modulating the excitation and plateau phases of the female sexual response on demand by oral administration of an effective amount of the agents.

The methods of the present invention are also useful in preparation for sexual intercourse by virtue of the ability to modulate the sexual response in both males and females.

The present invention is also directed to the use of a drug having activity for the manufacture of a medicament for oral administration to modify, on demand, the sexual response in a human and more particularly to improve erectile ability in response to sexual stimulation.

The formulations also eliminate the need for continuous therapy by providing a single dose for rapidly improving erectile ability on demand.

According to the present invention, the vasodilating agent is administered orally in the form of a rapidly dissolving tablet formulation, a rapidly dissolving chewable tablet formulation, solutions, effervescent formulations, and other orally administered formulations that permit the rapid introduction of the vasodilating substance to the circulation so as to improve erectile ability within a short time (on demand) after administration of a single dose of the agent.

Formulations and methods of the present invention are thus more convenient and help minimize any side-effects that may arise as a result of continuous or daily administration of the drugs. In addition, methods of the present invention allow more spontaneity in sexual activity than allowed by other methods such as the intracavernosal injection of vasodilators.

The above formulations are given by way of example and other rapidly dissolving formulations will be apparent to those of skill in the art.

The composition disclosed above includes specific amounts of the disclosed compounds, these amounts can be modified as required without departing from the spirit of the present invention. Additionally, the composition of the present invention can include additional compounds which do not alter the functionality of the composition of the present invention without departing from the spirit of the present invention.

The compound of the present invention is administered and dosed in accordance with good medical practice, taking into account the clinical condition of the individual patient, the site and method of administration, scheduling of administration, patient age, sex, body weight and other factors known to practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses may be single doses or multiple doses over a period of several days, but single doses are preferred.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to 10 mg/kg per day.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

What is claimed is:

1. A composition for boosting libido of an individual, said composition consisting essentially of an effective amount 667 mg Tribulus, 427 mg Muria Puama, 352 mg, Catuba Bark, 127 mg L-Arginine, 60 mg Avena Sativa, and 37 IU Vitamin E.

2. The composition according to claim 1, wherein the composition is delivered orally.

3. A spray composition for boosting libido of an individual, said composition consisting essentially of 35mg Tribulus terrestris, 30 mg Epimedium sagattatium, 10 mg Muria Puama, 10 mg Serenoa reopens, 10 mg Chrysin, and 4 mg 5-Androstenediol.

* * * * *